United States Patent
Yamaguchi et al.

(10) Patent No.: US 7,529,630 B2
(45) Date of Patent: May 5, 2009

(54) METHOD OF ANALYZING MASS ANALYSIS DATA AND APPARATUS FOR THE METHOD

(75) Inventors: Shinichi Yamaguchi, Kyoto (JP); Yusuke Inohana, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 264 days.

(21) Appl. No.: 11/730,983

(22) Filed: Apr. 5, 2007

(65) Prior Publication Data

US 2008/0073501 A1  Mar. 27, 2008

(30) Foreign Application Priority Data

Apr. 12, 2006  (JP) .............................. 2006-109962

(51) Int. Cl.
   *C12Q 1/04* (2006.01)
(52) U.S. Cl. .......................................... 702/27; 435/34
(58) Field of Classification Search ................. 250/281, 250/282; 702/27; 435/34
   See application file for complete search history.

(56) References Cited

U.S. PATENT DOCUMENTS 4,008,388 A * 2/1977 McLafferty et al. ........... 702/27
5,776,723 A * 7/1998 Herold et al. ................. 435/34

OTHER PUBLICATIONS

"Liquid Chromatograph-Mass Spectrometer—LCMS-IT-TOF" [online], Shimadzu Corporation, [Search Date: Apr. 6, 2006], Internet <http://www.an.shimadzu.co.jp/products/lcms/it-tof.htm>.

* cited by examiner

*Primary Examiner*—Kiet T Nguyen
(74) *Attorney, Agent, or Firm*—Westerman, Hattori, Daniels & Adrian, LLP.

(57) ABSTRACT

The present invention provides a method and an apparatus for analyzing mass analysis data for selecting a component similar to a target component quickly and accurately, based on $MS^n$ analysis for each unknown component in the sample. First, $MS^n$ analysis is performed for each of the components in the mixed sample, and based on the obtained spectral data (measured data) and the spectral data of the target component (reference data), predetermined parameters are extracted (Step S11 to S13). Next, by multivariable analysis of the parameters, the similarity between the target component and each of the components in the mixed sample is evaluated (Step S14). Finally, based on the similarity value, components similar to the target component are selected (Step S16).

12 Claims, 6 Drawing Sheets

| | 1 | 2 | 3 | 4 | 5 | 6 | 7 | 8 |
|---|---|---|---|---|---|---|---|---|
| 1 | Primary ID | m/z | P#1 | P#2 | P#3 | P#4 | P#5 | P |
| 2 | PrecRT | | 5.05333 | 5.16333 | 5.25333 | 5.34667 | 5.46333 | 5.563 |
| 3 | PrecMZ | | 327.077 | 371.312 | 235.163 | 280.096 | 205.081 | 235.1 |
| 4 | I#1 | 100.058 | -0.0752462 | -0.0309372 | -0.0490892 | -0.0309898 | -0.0482617 | -0.03613 |
| 5 | I#2 | 100.115 | -0.0752462 | -0.0309372 | -0.0490892 | -0.0309898 | -0.0482617 | -0.03613 |
| 6 | I#3 | 102.08 | -0.0752462 | -0.0309372 | -0.0490892 | -0.0309898 | -0.0482617 | -0.03613 |
| 7 | I#4 | 102.088 | -0.0752462 | -0.0309372 | -0.0490892 | -0.0309898 | -0.0482617 | -0.03613 |
| 8 | I#5 | 102.096 | -0.0752462 | -0.0309372 | -0.0490892 | -0.0309898 | -0.0482617 | -0.03613 |
| 9 | I#6 | 102.566 | -0.0752462 | -0.0309372 | -0.0490892 | -0.0309898 | -0.0482617 | -0.03613 |
| 10 | I#7 | 103.047 | -0.0752462 | -0.0309372 | -0.0490892 | -0.0309898 | -0.0482617 | -0.03613 |
| 11 | I#8 | 103.087 | -0.0752462 | -0.0309372 | -0.0490892 | -0.0309898 | -0.0482617 | -0.03613 |
| 12 | I#9 | 105.034 | -0.0752462 | -0.0309372 | -0.0490892 | -0.0309898 | -0.0482617 | -0.03613 |
| 13 | I#10 | 105.048 | -0.0752462 | -0.0309372 | -0.0490892 | -0.0309898 | -0.0482617 | -0.03613 |
| 14 | I#11 | 105.058 | -0.0752462 | -0.0309372 | -0.0490892 | -0.0309898 | -0.0482617 | -0.03613 |
| 15 | I#12 | 105.07 | -0.0752462 | -0.0309372 | -0.0490892 | -0.0309898 | -0.0482617 | -0.03613 |
| 16 | I#13 | 105.081 | -0.0752462 | -0.0309372 | -0.0490892 | -0.0309898 | -0.0482617 | -0.03613 |
| 17 | I#14 | 105.492 | -0.0752462 | -0.0309372 | -0.0490892 | -0.0309898 | -0.0482617 | -0.03613 |
| 18 | I#15 | 105.644 | -0.0752462 | -0.0309372 | -0.0490892 | -0.0309898 | -0.0482617 | -0.03613 |
| 19 | I#16 | 106.062 | -0.0752462 | -0.0309372 | -0.0490892 | -0.0309898 | -0.0482617 | -0.03613 |
| 20 | I#17 | 106.066 | -0.0752462 | -0.0309372 | -0.0490892 | -0.0309898 | -0.0482617 | -0.03613 |
| 21 | I#18 | 106.073 | -0.0752462 | -0.0309372 | -0.0490892 | -0.0309898 | -0.0482617 | -0.03613 |
| 22 | I#19 | 107.047 | -0.0752462 | -0.0309372 | 18.3959 | -0.0309898 | -0.0482617 | -0.03613 |

Fig. 7

<PCA METHOD>

Fig. 8
<PLS METHOD>

Fig. 9
<HCA METHOD>

Fig. 10

| EXPECTED MASS | RT (MINUTES) | COMPARATIVE EXAMPLE | EMBODIMENT |
|---|---|---|---|
| 457.0759 | 33,37,42 | FOUND | FOUND |
| 5311287 | | NOT FOUND | NOT FOUND |
| 360.756 | 14.5,39.5 | FOUND (14.5 was incorrect) | ◎ (FOUND ONLY 39.5 ) |
| 230.0494 | 25.5 | FOUND | FOUND |
| 524.0334 | 15 | FOUND | FOUND |
| 860.1546 | | NOT FOUND | NOT FOUND |
| 231.112 | | NOT FOUND | NOT FOUND |
| 429.0964 | 23,31.5 | FOUND (probably incorrect) | ◎(NOT FOUND) |
| 116.1011 | | NOT FOUND | FOUND |
| 674.0906 | | NOT FOUND | FOUND |

METHOD OF ANALYZING MASS ANALYSIS DATA AND APPARATUS FOR THE METHOD

The present invention relates to a method of analyzing mass analysis data for analyzing data obtained by an $MS^n$ analysis in which parent ions originating from a sample to be analyzed are dissociated into daughter ions once or multiple times. More specifically, the invention relates to a method of selecting a component similar to a target component from unknown components in the sample, and a method of deducing the molecular structure of the selected unknown component. Also, the present invention relates to an apparatus for performing the method.

BACKGROUND OF THE INVENTION

Conventionally, chromatograph-mass spectrometers such as liquid chromatograph-mass spectrometers (LC/MS) and gas chromatograph-mass spectrometers (GC/MS) have been preferably used to analyze a sample which contains multiple components. Some mass spectrometers can operate an $MS^n$ analysis in which ions are captured and dissociated successively once or multiple times (refer to Non-Patent Document 1 for example) to obtain structural information of sample components separated by chromatography.

When performing an analysis of a mixed sample's component which is similar to a known component, it is first necessary to obtain $MS^n$ analysis data of the mixed sample, and then based on that data, select a molecular (component) which has a similar structure to that of a target molecule from many components contained in the sample. This kind of analysis includes, for example, quantitative determination and/or structural analysis of metabolites in the pharmacokinetics studies, and identification of analogous impurities of by-products and/or decomposition products in the synthesis of pharmaceutical compounds.

In the conventional analysis, every $MS^n$ spectrum (e.g. $MS^2$ spectrum) obtained for each peak in the chromatogram of a sample is shown one by one on a monitor. An operator looks at the monitor and judges the similarity between the spectrum and the $MS^n$ spectrum of the known substance to be targeted by visual comparison. Then the operator selects a candidate for the similar component.

[Non-Patent Document 1] "Liquid Chromatograph-Mass Spectrometer—LCMS-IT-TOF", [online], Shimadzu Corporation, [Search Date: Apr. 6, 2006], Internet <http://www.an-.shimadzu.co.jp/products/lcms/it-tof.htm>

Unfortunately, only a skilled operator with much knowledge and experience can do a manual analysis as described earlier. In addition, since visibly checking every single $MS^n$ spectrum obtained from each component requires a huge amount of time and effort, it is difficult to enhance the efficiency of the analysis.

To solve the above-described problem, the present invention intends to provide a method of analyzing mass analysis data for quickly and accurately searching a component similar to a target component based on a result of an $MS^n$ analysis for each unknown component in a sample.

SUMMARY OF THE INVENTION

Thus, the present invention provides a method of analyzing mass analysis data for selecting a component similar to a target component from one or more unknown sample components, based on a result of an $MS^n$ analysis in which a precursor ion originating from each of the sample components is dissociated into fragment ions by (n−1) steps (where $n \geqq 2$) and then the fragment ions are subjected to a mass-analyzing process, wherein the method comprises:

a) an extraction step for extracting predetermined parameters from spectral data obtained by the $MS^n$ analysis and $MS^n$ spectral data of the target component;

b) a similarity evaluation step for evaluating a similarity value between the target component and each of the sample components by multivariable analysis of the parameters; and c) a selecting step for selecting a component similar to the target component based on the similarity value.

The method of analyzing mass analysis data according to the present invention can obtain at one time each similarity value of all the components contained in a sample, by multivariable analysis using data obtained by an $MS^n$ analysis for each component in the sample. Thus, a component similar to a known substance can be easily selected out from a large quantity of data without manually comparing the $MS^n$ spectra.

The present invention also provides an apparatus for analyzing mass analysis data for selecting a component similar to a target component from one or more unknown sample components, based on a result of an $MS^n$ analysis in which a precursor ion originating from each of the sample components is dissociated into fragment ions by (n−1) steps (where $n \geqq 2$) and then the fragment ions are subjected to a mass-analyzing process, wherein the apparatus comprises:

a) a measured data retriever for retrieving spectral data of each of the sample components obtained by the $MS^n$ analysis;

b) a target component data collector for collecting existing $MS^n$ spectral data of the target component;

c) a parameter extractor for extracting predetermined parameters from spectral data obtained by the measured data retriever and the target component data collector; and d) a similarity evaluator for evaluating a similarity value between each of the sample components and the target component by multivariable analysis of the parameters.

EXPLANATION OF NUMERALS

10 . . . Data Analyzing Apparatus
11 . . . Central Control Unit
12 . . . Spectral Data Creator
13 . . . Analyzing Processor
14 . . . Measured Data Memory Unit
15 . . . Reference Data Memory Unit
21 . . . Measured Data Retriever
22 . . . Target Component Data Collector
23 . . . Parameter Extractor
24 . . . Similarity Evaluator
25 . . . Grouping Means
30 . . . LC/MS
40 . . . Input Unit
50 . . . Monitor

DETAILED DESCRIPTION OF PREFERRED EMBODIMENTS

An embodiment of the apparatus for analyzing mass analysis data (data analyzing apparatus), which carries out an analysis by a method of analyzing mass analysis data according to the present invention, is described with reference to the drawings. Although a liquid chromatograph-mass spectrometer is used in this embodiment, other types of chromatograph-mass spectrometers such as a gas chromatograph-mass spectrometer can be used alternatively.

Figure 1:
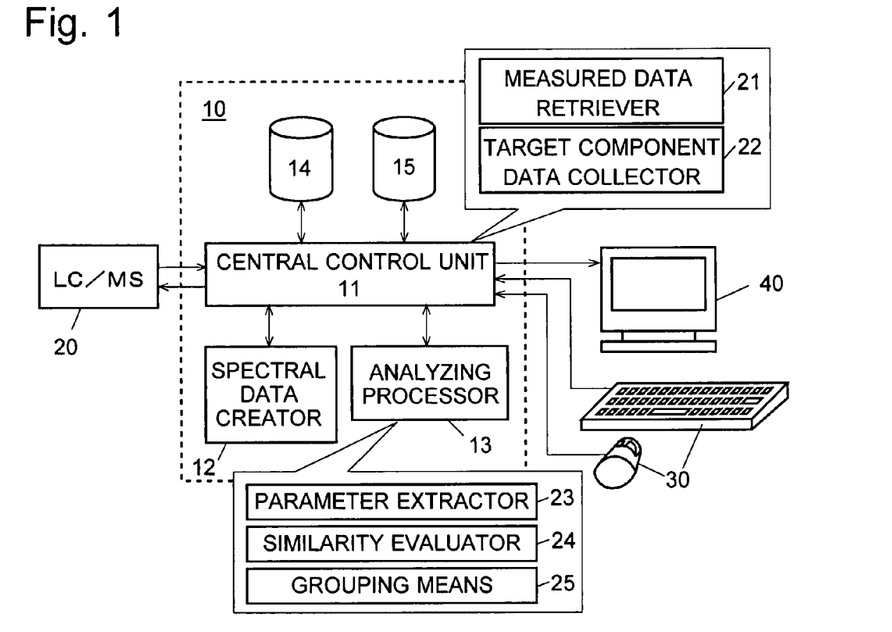
FIG. 1 is a schematic diagram of the apparatus for data analyzing apparatus according to an embodiment of the present invention.

FIG. 1 is a schematic diagram of the apparatus for the data analyzing apparatus 10 of the present embodiment. The data analyzing apparatus 10 processes detected data delivered from LC/MS 30. The data analyzing apparatus 10 contains a central control unit 11, a spectral data creator 12, an analyzing processor 13, a measured data memory unit 14, and a reference data memory unit 15. Both the measured data memory unit 14 and the reference data memory unit 15 are connected to the central control unit 11. An input unit 40 and a monitor 50 are connected to the central control unit 11. The central control unit 11 has functions to control the operation of LC/MS 30.

The central control unit 11, the spectral data creator 12, and the analyzing processor 13 are realized by a CPU (Central Processing Unit) running a specific application program. The central control unit 11 contains a measured data retriever 21 and a target component data collector 22, both of which are realized by the CPU running the specific program. The analyzing processor 13 contains a parameter extractor 23, a similarity evaluator 24, and a grouping means, all of which are also realized by the CPU running the specific program.

The measured data memory unit 14 is a read/write storage device such as a hard disk drive or magnetooptic (MO) disc drive. The reference data memory unit 15 can be a hard disk drive, or read-only device such as a CD-ROM drive if no data is to be written to the reference data memory unit 15. In the reference data memory unit 15, various data relevant to compounds (e.g. structural formulas, compositional formulas, and $MS^n$ spectrum data) are stored. An operator can specify a target compound from the stored compounds by operating the input unit 40 when searching for a similar compound. Although the measured data memory unit 14 and the reference data memory unit 15 are shown independently in FIG. 1, it is possible to use a single storage device, such as a hard disk drive, which has logical segments. The input unit 40 includes a keyboard and/or mouse, and the monitor 50 includes a cathode ray tube (CRT) and/or printer.

The data analyzing apparatus 10 can be realized as an operating/analyzing unit for LC/MS only, or as a general computer system such as a personal computer in which a program for performing the analysis method of the present invention is installed.

The LC/MS 30 consists of a liquid chromatograph having a column for temporally separating a mixed sample, and a mass spectrometer capable of an $MS^n$ (at least $MS^2$) analysis. As a mass spectrometer of this kind, it is possible, for example, to use a triple quadrupole mass spectrometer or an ion trap mass spectrometer. Sample components eluted from the column of the chromatograph are sequentially ionized by the mass spectrometer and then analyzed using the $MS^n$ analysis. Ions having a proper mass-to-charge ratio are selected as precursor ions automatically from ions originating from each of the sample components. The precursor ions are dissociated into fragment ions, and the fragment ions are mass-separated and detected. The selection, dissociation, and detection of the ions can be repeated, if necessary, multiple times.

While the sample is being measured, detected data (digitized detected signals) regarding electric current according to the number of ions detected at each mass-to-charge ratio is sent from the LC/MS 30 to the data analyzing apparatus 10. The spectral data creator 12 calculates spectral data, in which a mass-to-charge ratio and peak intensity at the mass-to-charge ratio (relative signal intensity) are paired, by processing the detected data in accordance with a predetermined algorithm. The spectral data is then stored in the measured data memory unit 14. Also, a total ion chromatogram (TIC) is produced based on the spectral data obtained by an $MS^1$ analysis in which no dissociating operation is performed, and the total ion chromatogram is stored in the measured data memory unit 14.

Figure 2:
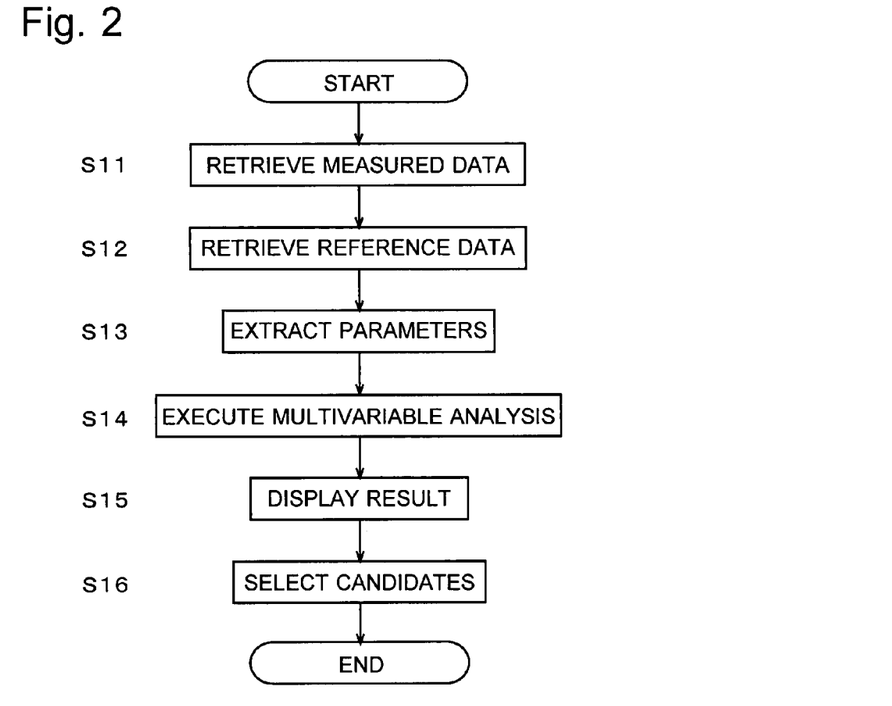
FIG. 2 is a flow chart showing an example of the characteristic steps of the analysis process for selecting the candidates for the similar component according to the present embodiment.

Next, an analysis process which is carried out after the sample is measured is described with reference to the flow chart shown in FIG. 2. First, the central control unit 11 (the measured data retriever 21) retrieves spectral data (spectral data obtained at each step of the $MS^n$ analysis) which corresponds to each peak on the TIC from the measured data memory unit 14. The central control unit 11 (the target component data collector 22) also retrieves spectral data of the target component specified by the operator from the reference data memory unit 15. The central control unit 11 then sends the spectral data and the spectral data of the target component to the analyzing processor 13 (Step S11, S12).

Based on the spectral data, the analyzing processor 13 (the parameter extractor 23) extracts parameters for the multivariable analysis, which is to be described later, and creates a table of the parameters (Step S13). The preferable parameters for the multivariable analysis are, for example, at least one of the following; (1) a mass of a fragment ion at each dissociating step of an $MS^n$ analysis, (2) a difference between a mass of a fragment ion and a mass of the precursor ion at each dissociating step of an $MS^n$ analysis, (3) a difference between a mass of a fragment ion at each dissociating step of an $MS^n$ analysis and a mass of a fragment ion or a precursor ion at the previous step, which were original ions of the fragment ion, (4) an isotopic distribution pattern of a precursor ion.

Next, the analyzing processor 13 (the similarity evaluator 24) executes the multivariable analysis based on the table, and evaluates one or more similarity values between each of the sample components and the target component (Step S14). As a method for the multivariable analysis, it is possible to use Hierarchical Cluster Analysis (HCA), Principal Component Analysis (PCA), or Partial Least Squares (PLS), however, it is not limited to them.

In the next step, the result of the multivariable analysis executed by the analyzing processor 13 is shown on the monitor 50 (Step S15), and candidates for the similar component are selected based on the result (Step S16). In the Step S16, the operator looks at the results shown on the monitor 50 and selects a candidate for the similar component. Or, instead, the data analyzing apparatus 10 automatically selects a component which has a higher similarity value than a predetermined threshold, and displays the component on the monitor 50.

Figure 3:
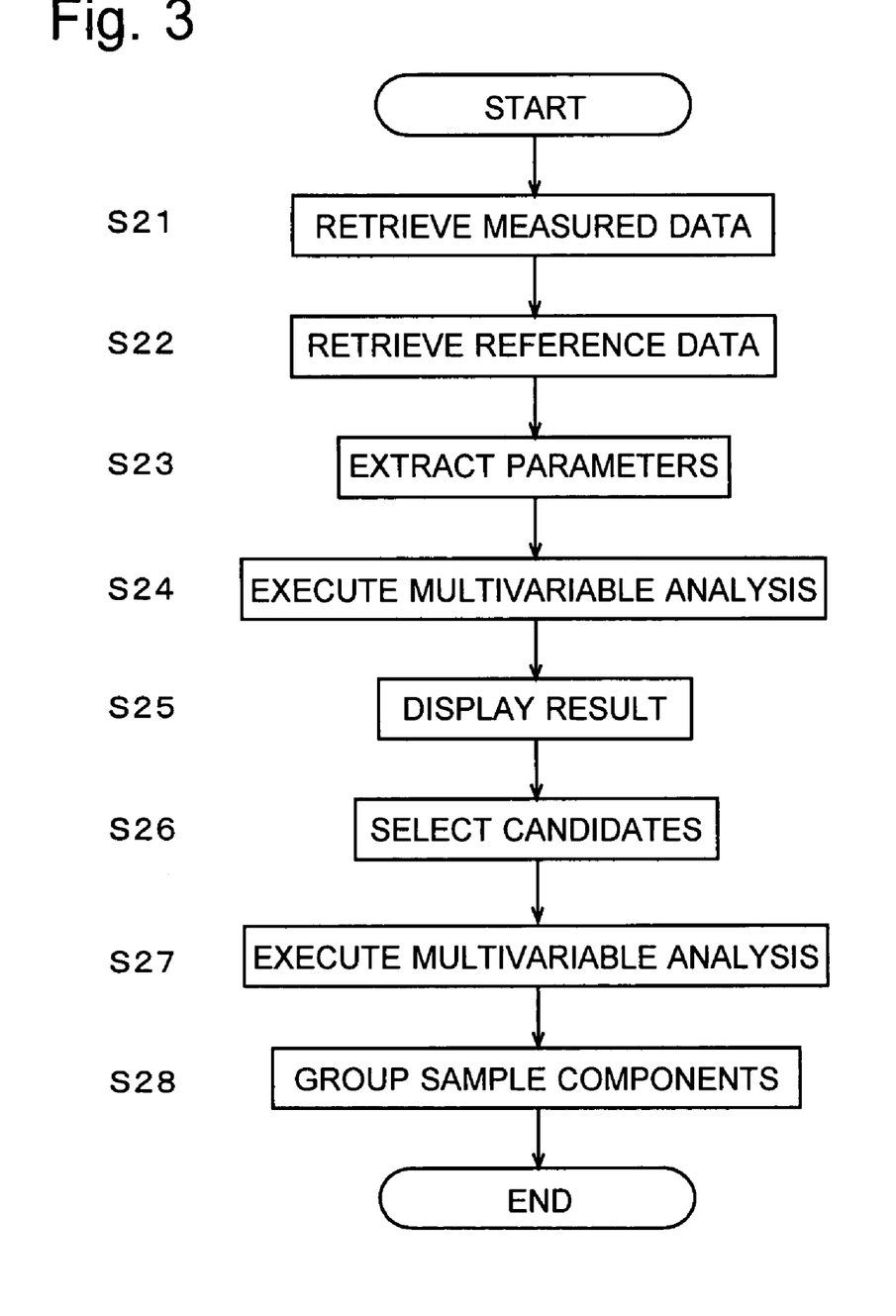
FIG. 3 is a flow chart showing another example of the characteristic steps of the analysis process for selecting the candidates for the similar component according to the present embodiment.

In the method of analyzing mass analysis data according to the present invention, it is preferable to group the components, which were selected as candidates for the similar components by the multivariable analysis, and the target component by their characteristics. The grouping can be performed by executing the multivariable analysis once more using the parameters. An exemplary embodiment is described with reference to FIG. 3. FIG. 3 is a flow chart showing an example of the characteristic steps of the analysis process including the grouping step. The steps S21 through S26 of the flow chart in FIG. 3 are equal to the steps S11 through SI 6 of the flow chart in FIG. 2, however the flow chart in FIG. 3 has extra steps, Step S27 and S28. After candidates for the similar component are selected in the step S26, the analyzing processor 13 (the grouping means 25 in FIG. 1) evaluates a similarity value, by multivariable analysis of the parameters obtained in the step S23, between the target component and the sample components selected in the step S26 (Step S27). In the next step, the analyzing processor 13 then groups the sample components based on the similarity values evaluated in the step S 27 (Step S28).

According to this method, information on each of the groups can be obtained, such as (1) peaks existing in the group, and existing also in the target component, (2) peaks existing in the group, and not existing in the target component, and (3) peaks not existing in the group, and existing in the target component. The information (1) shows that there is a structure in common between the unknown substances belonging to the group and the known substance to be targeted. Based on this information, it is possible to evaluate how similar the structure of each candidate is to the structure of the known substance. The information (2) shows the common structural change within the group, and the information (3) shows that the structure corresponding to the peak is lost in each of the components within the group. Thus, grouping each component by its characteristic by executing the multivariable analysis once more for the selected candidates, it is possible to obtain useful data for estimating the structure of the unknown component from the structure of the known substance (target substance).

Figure 4A:
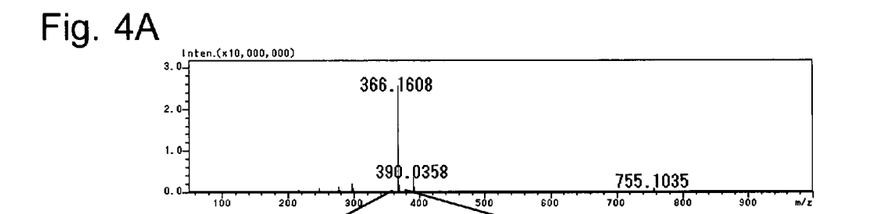
FIG. 4A is an MS spectrum of the target component.
Figure 4B:
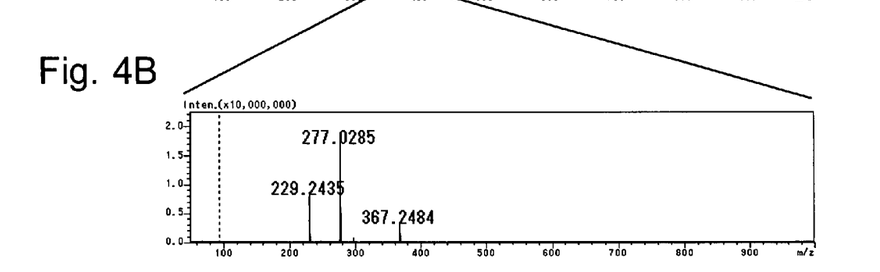
FIG. 4B is an MS/MS spectrum of the target component.

This section describes an example of the analysis using the method of analyzing mass analysis data according to the present invention. An MS spectrum and an MS/MS spectrum (obtained by dissociating the m/z=366.1608 peak on the MS spectrum) of a target component (known substance) are respectively shown in FIG. 4A and FIG. 4B. First, a mixed sample (biological sample including the target component and its metabolites) was separated temporally by a liquid chromatograph. The components eluted from the column of the chromatograph were analyzed sequentially using the MS/MS (MS$^2$) analysis, and then the components similar to the target component were searched using the obtained data.

Figures 5A, 5B:
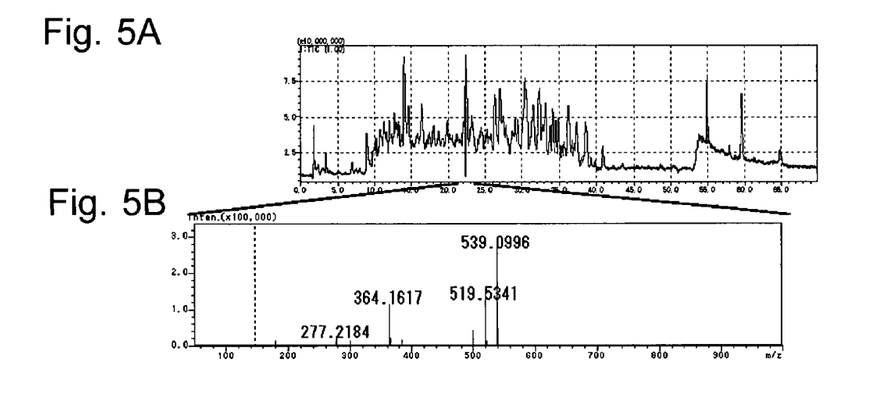
FIG. 5A is a total ion chromatogram (TIC) of the sample according to the present embodiment.
FIG. 5B is an MS/MS spectrum of a peak in the TIC of FIG. 5A.
Figure 6:
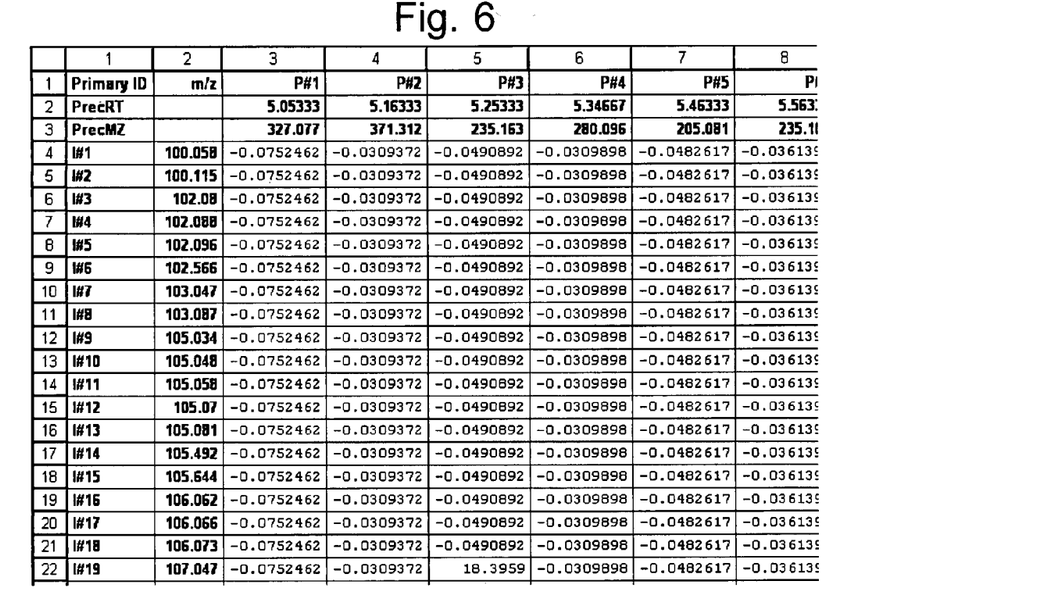
FIG. 6 is a table of the predetermined information.

FIG. 5A is a Total Ion Chromatogram (TIC) of the sample obtained by the analysis. In this embodiment, an MS/MS analysis was carried out for dissociated precursor ions selected automatically at each of the peaks on the TIC. One example of the MS/MS spectrum is shown in FIG. 5B. FIG. 6 shows a table of the predetermined information according to the MS$^1$ spectral data and MS$^2$ spectral data obtained by the analysis and also according to the existing MS$^1$ and MS$^2$ spectral data of the target component. In the table in FIG. 6, P#1, P#2, . . . mean variable names of the precursor ions corresponding to each of the peaks on the TIC, PrecRT means the time each of the precursor ions were measured, PrecMZ means the mass-to-charge ratio of each precursor ion, I#1, I#2, . . . mean the mass-to-charge ratios of the fragment ions dissociated from each of the precursor ions and also mean the differences of the mass-to-charge ratios between the precursor ions and each fragment ion. The numbers in the table in FIG. 6 shows standardized intensities.

Figure 7:
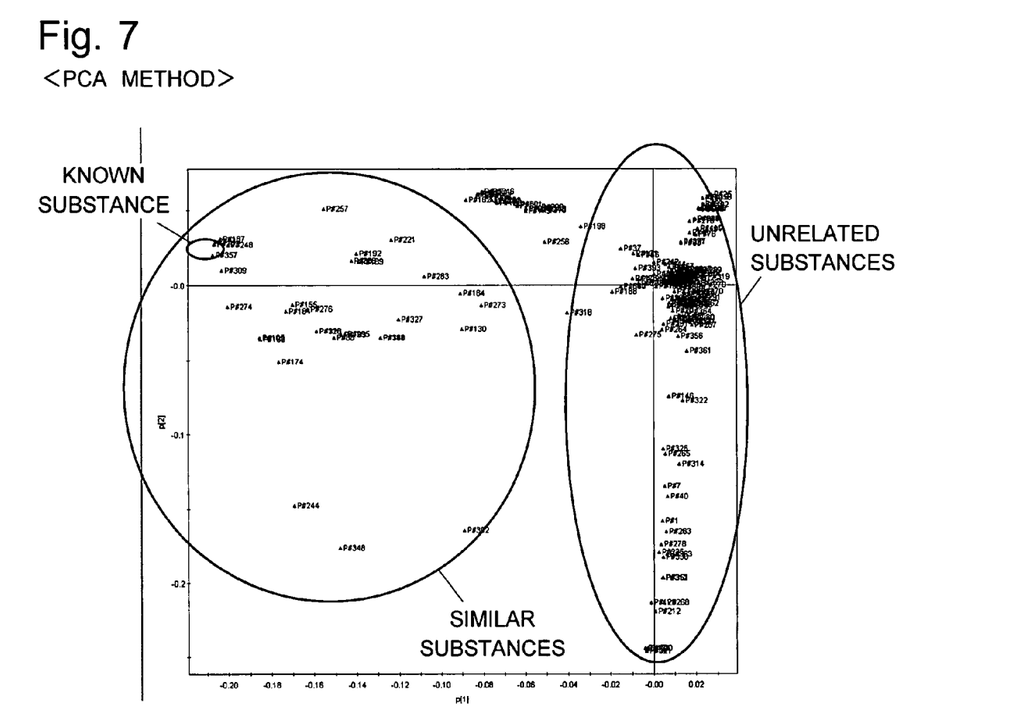
FIG. 7 is a diagram showing a result of multivariable analysis using the PCA method.
Figure 8:
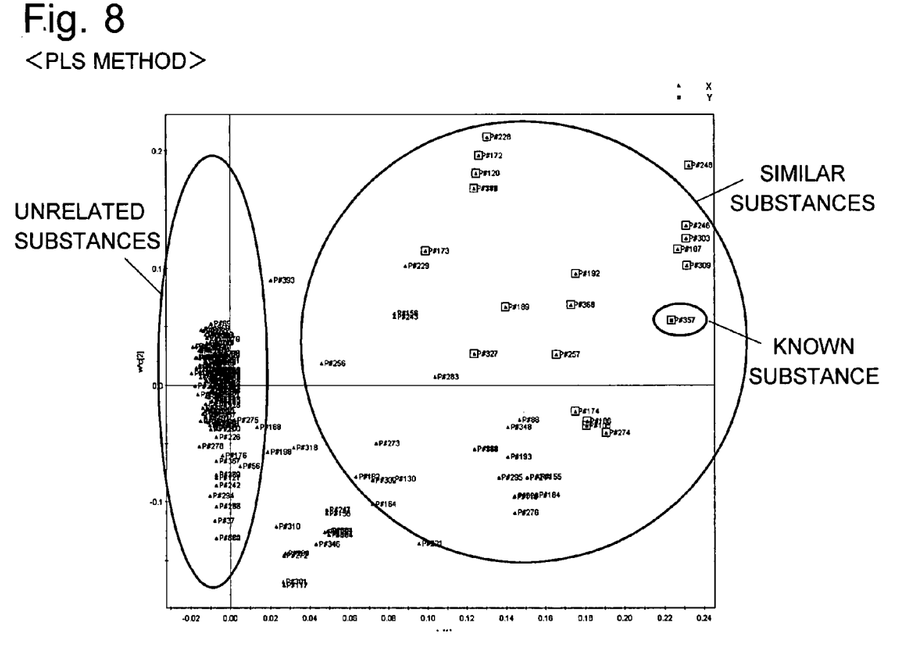
FIG. 8 is a diagram showing a result of multivariable analysis using the PLS method.
Figure 9:
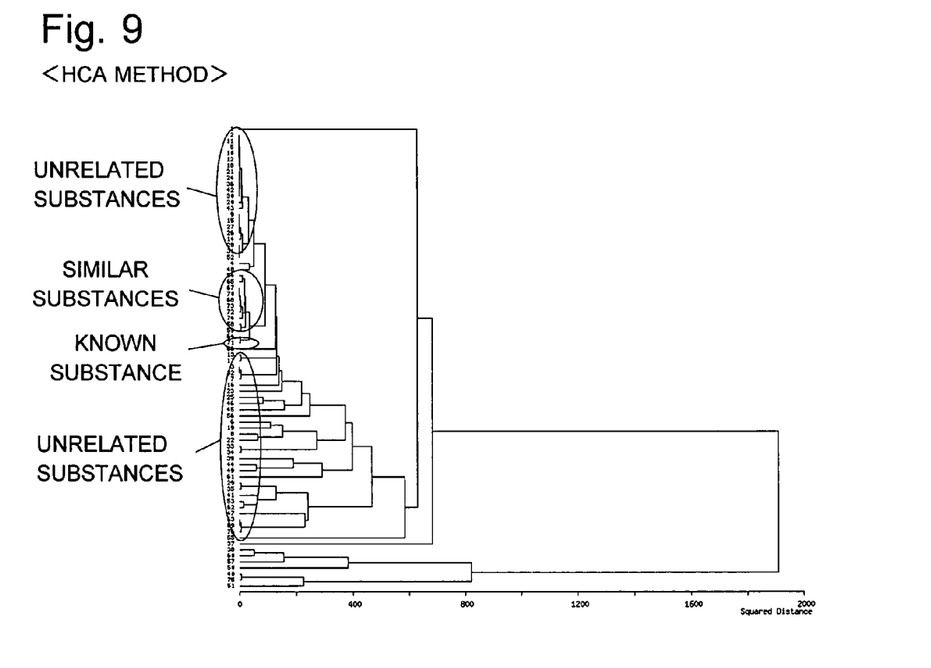
FIG. 9 is a diagram showing a result of multivariable analysis using the HCA method.
Figure 10:
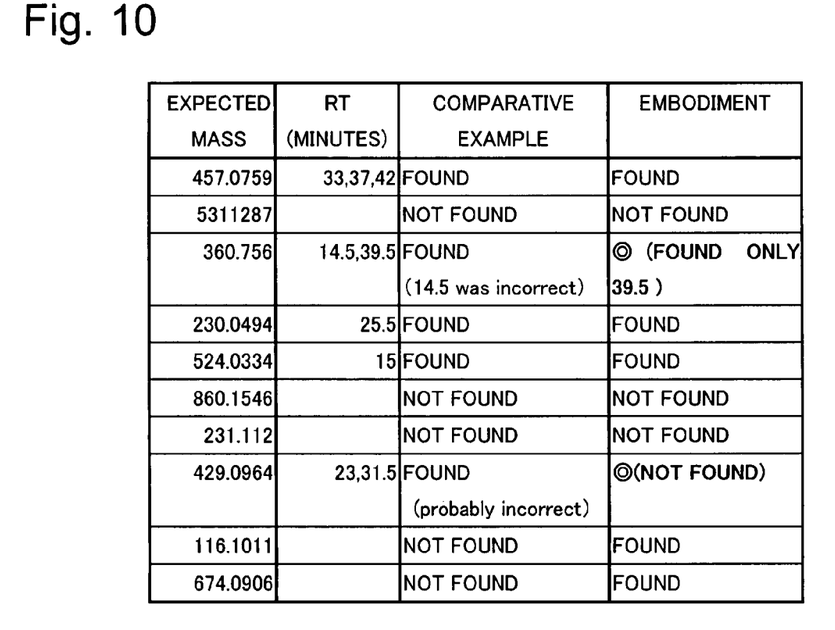
FIG. 10 is a table showing a comparison between the analysis result by multivariable analysis and the result of a manual analysis for the same data.

FIGS. 6 to 8 show the results of several multivariable analysis methods based on the table. FIG. 7 is a result by the PCA method, FIG. 8 is a result by the PLS method, and FIG. 9 is a result by the HCA method. The table shown in FIG. 10 is a comparison between the analysis result by multivariable analysis and the result of a manual analysis for the same data. "Expected mass" in FIG. 10 means an expected mass when assuming that known structural changes in the target component have occurred. As shown in FIG. 10, all the components found by manual analysis ("comparative example" in FIG. 10) were selected by the analysis method according to the present embodiment ("embodiment" in FIG. 10). Furthermore, many candidates that were not found by manual analysis were found by the analysis method according to the present embodiment. In addition, although it took about two days to analyze manually, it took only a few seconds to finish the analysis according to the present embodiment.

As described above, by an analysis using the method of analyzing mass analysis data according to this embodiment, it is possible to reduce the time and effort required to analyze compared to the conventional manual method. The accuracy of the analysis according to the embodiment was the same or more than the manual method.

Finally, it should be noted that the embodiment described thus far is a mere example, which can be changed, modified or expanded within the sprit of the present invention. For example, the present invention can be applied for the analysis based on data of MS$^n$ analysis having two or more dissociating steps.

What is claimed is:

1. A method of analyzing mass analysis data for selecting a component similar to a target component from one or more unknown sample components, based on a result of an MS$^n$ analysis in which a precursor ion originating from each of the sample components is dissociated into fragment ions by (n−1) steps (where n≧2) and then the fragment ions are subjected to a mass-analyzing process, wherein the method comprises:

a) an extraction step for extracting predetermined parameters from spectral data obtained by the MS$^n$ analysis and MS$^n$ spectral data of the target component;

b) a similarity evaluation step for evaluating a similarity value between the target component and each of the sample components by multivariable analysis of the parameters; and c) a selecting step for selecting a component similar to the target component based on the similarity value.

2. The method of analyzing mass analysis data according to claim 1, wherein, the parameters are at least one of the following:

a mass of a fragment ion at each dissociating step of an MS$^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

3. A method of analyzing mass analysis data for selecting a component similar to a target component from one or more unknown sample components, based on a result of an $MS^n$ analysis in which a precursor ion originating from each of the sample components is dissociated into fragment ions by (n−1) steps (where n≧2) and then the fragment ions are subjected to a mass-analyzing process, wherein the method comprises:

a) an extraction step for extracting predetermined parameters from spectral data obtained by the $MS^n$ analysis and $MS^n$ spectral data of the target component;

b) a similarity evaluation step for evaluating a similarity value between the target component and each of the sample components by multivariable analysis of the parameters;

c) a selecting step for selecting a component similar to the target component based on the similarity value;

d) a second similarity evaluation step for evaluating a similarity value between the target component and the sample components selected in the step c), by multivariable analysis of the parameters; and e) a grouping step for grouping the sample components based on the similarity values evaluated in the step d).

4. The method of analyzing mass analysis data according to claim 3, wherein, the parameters are at least one of the following:

a mass of a fragment ion at each dissociating step of an $MS^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

5. An apparatus for analyzing mass analysis data for selecting a component similar to a target component from one or more unknown sample components, based on a result of an $MS^n$ analysis in which a precursor ion originating from each of the sample components is dissociated into fragment ions by (n−1) steps (where n≧2) and then the fragment ions are subjected to a mass-analyzing process, wherein the apparatus comprises:

a) a measured data retriever for retrieving spectral data of each of the sample components obtained by the $MS^n$ analysis;

b) a target component data collector for collecting existing $MS^n$ spectral data of the target component;

c) a parameter extractor for extracting predetermined parameters from spectral data obtained by the measured data retriever and the target component data collector; and d) a similarity evaluator for evaluating a similarity value between each of the sample components and the target component by multivariable analysis of the parameters.

6. The apparatus for analyzing mass analysis data according to claim 5, wherein, the parameters are at least one of the following:

a mass of a fragment ion at each dissociating step of an $MS^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

7. An apparatus for analyzing mass analysis data for selecting a component similar to a target component from one or more unknown sample components, based on a result of an $MS^n$ analysis in which a precursor ion originating from each of the sample components is dissociated into fragment ions by (n−1) steps (where n≧2) and then the fragment ions are subjected to a mass-analyzing process, wherein the apparatus comprises:

a) a measured data retriever for retrieving spectral data of each of the sample components obtained by the $MS^n$ analysis;

b) a target component data collector for collecting existing $MS^n$ spectral data of the target component;

c) a parameter extractor for extracting predetermined parameters from spectral data obtained by the measured data retriever and the target component data collector;

d) a similarity evaluator for evaluating a similarity value between each of the sample components and the target component by multivariable analysis of the parameters; and e) a grouping means for evaluating, by multivariable analysis of the parameters, a similarity value between the target component and a plurality of the sample components selected as similar to the target component, and then grouping the sample components based on the similarity values.

8. The apparatus for analyzing mass analysis data according to claim 7, wherein, the parameters are at least one of the following:

a mass of a fragment ion at each dissociating step of an $MS^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

9. A mass analysis data analyzing program for operating a computer as an apparatus for analyzing mass analysis data for selecting a component similar to a target component from one or more unknown sample components, based on a result of an $MS^n$ analysis in which a precursor ion originating from each of the sample components is dissociated into fragment ions by (n−1) steps (where n≧2) and then the fragment ions are subjected to a mass-analyzing process, comprising:

a) a measured data retriever for retrieving spectral data of each of the sample components obtained by the $MS^n$ analysis;

b) a target component data collector for collecting existing $MS^n$ spectral data of the target component;

c) a parameter extractor for extracting predetermined parameters from spectral data obtained by the measured data retriever and the target component data collector; and d) a similarity evaluator for evaluating a similarity value between each of the sample components and the target component by multivariable analysis of the parameters.

10. The mass analysis data analyzing program according to claim 9, wherein, the parameters are at least one of the following:

a mass of a fragment ion at each dissociating step of an $MS^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

11. A mass analysis data analyzing program for operating a computer as an apparatus for analyzing mass analysis data for selecting a component similar to a target component from one or more unknown sample components, based on a result of an $MS^n$ analysis in which a precursor ion originating from each of the sample components is dissociated into fragment ions by (n−1) steps (where n≧2) and then the fragment ions are subjected to a mass-analyzing process, comprising:

a) a measured data retriever for retrieving spectral data of each of the sample components obtained by the $MS^n$ analysis;

b) a target component data collector for collecting existing $MS^n$ spectral data of the target component;

c) a parameter extractor for extracting predetermined parameters from spectral data obtained by the measured data retriever and the target component data collector;

d) a similarity evaluator for evaluating a similarity value between each of the sample components and the target component by multivariable analysis of the parameters; and e) a grouping means for evaluating, by multivariable analysis of the parameters, a similarity value between the target component and a plurality of the sample components selected as similar to the target component, and then grouping the sample components based on the similarity values.

12. The mass analysis data analyzing program according to claim 11, wherein, the parameters are at least one of the following:

a mass of a fragment ion at each dissociating step of an $MS^n$ analysis;

a difference between a mass of a fragment ion and a mass of a precursor ion at each dissociating step of an $MS^n$ analysis;

a difference between a mass of a fragment ion at each dissociating step of an $MS^n$ analysis and a mass of a fragment ion or a precursor ion at a previous step, which were original ions of the fragment ion; and an isotopic distribution pattern of a precursor ion.

\* \* \* \* \*